United States Patent [19]

Verweij

[11] 4,000,129
[45] Dec. 28, 1976

[54] 6-AMINOPENICILLANIC ACID SULFOXIDE SILYL ESTERS
[75] Inventor: Jan Verweij, Leiden, Netherlands
[73] Assignee: Koninklijke Nederlandsche Gist-en spiritusfabriek N.V., Delft, Netherlands
[22] Filed: Aug. 26, 1974
[21] Appl. No.: 500,261

Related U.S. Application Data

[60] Continuation-in-part of Ser. No. 341,498, March 15, 1973, abandoned, which is a division of Ser. No. 115,883, Feb. 16, 1971, Pat. No. 3,852,281.

[30] Foreign Application Priority Data

Feb. 18, 1970 United Kingdom ............... 7892/70
July 23, 1970 United Kingdom ............ 35769/70

[52] U.S. Cl. .......................................... 260/239.1
[51] Int. Cl.$^2$ ...................................... C07D 499/32
[58] Field of Search ................................ 260/239.1

[56] References Cited
UNITED STATES PATENTS

| 3,507,861 | 4/1970 | Morin et al. ............... 260/243 C |
| 3,531,469 | 9/1970 | Bamberg et al. ............ 260/239.1 |
| 3,654,266 | 4/1972 | Robinson ................... 260/239.1 |

Primary Examiner—Paul M. Coughlin, Jr.
Attorney, Agent, or Firm—Hammond & Littell

[57] ABSTRACT

Novel 6-substituted amino-penicillanic sulfoxide silyl esters useful as intermediates for the preparation of 7-aminodesacetoxycephalosporanic acids derivatives.

13 Claims, No Drawings

6-AMINOPENICILLANIC ACID SULFOXIDE SILYL ESTERS

PRIOR APPLICATIONS

This application is a continuation-in-part of application Ser. No. 341,498 filed Mar. 15, 1973, now abandoned which in turn is a division of U.S. patent application Ser. No. 115,883 filed Feb. 16, 1971 now U.S. Pat. No. 3,852,281.

STATE OF THE ART

U.S. Pat. No. 3,275,626 describes the preparation of 7-aminocepham derivatives by heating analogous 6-aminopenicillanic sulfoxide derivatives in solution to temperatures of about 80° to 175° C under acid conditions, which may be promoted by, for example, acetic anhydride, or p-toluene-sulfonic acid. This process involving heating under acid conditions results in a rearrangement of the heterocyclic ring structure leading to the formation among others of a thiazine ring which is a structural part of cephalosporin compounds. Several of these cephalosporin compounds possess useful antibiotic activity and are, therefore, very important as therapeutics.

On the other hand, it has been disclosed by Morin et al. [J.A.C.S., Vol. 91 (1969), p. 1401-7] that heating esters of 6-aminopenicillanic sulfoxide derivatives such as the cyanomethyl and methyl esters of phenoxymethylpenicillin sulfoxide in the presence of bases such as triethylamine and pyridine causes fission of the bicyclic ring system and results in the formation of isothiazolone derivatives.

OBJECTS OF THE INVENTION

It is an object of the invention to provide a novel process for the preparation of silyl esters of 6-substituted aminopenicillanic acid compounds.

It is a further object of the invention to provide novel silyl esters of 6-aminopenicillanic sulfoxides.

These and other objects and advantages of the invention will become obvious from the following detailed description.

THE INVENTION

The novel penicillanic acid sulfoxide silyl esters have the formula

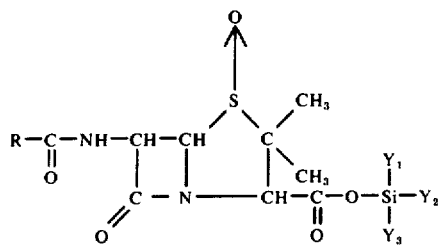

wherein R is selected from the group consisting of benzyl (wherein the methylene group may be substituted by amino or benzyloxycarbamoyl), phenoxymethyl and naphthyl optionally substituted with ethoxy, and $Y_1$, $Y_2$ and $Y_3$ are the same or different and are individually selected from the group consisting of halogen, alkyl of 1 to 4 carbon atoms optionally substituted with halogen, phenyl and 6-substituted aminopenicillanyl sulfoxide carbonyloxy group according to the group which is attached to the silicon atom in the above formula, wherein R is as hereinbefore defined.

Preferred compounds are compounds of formula I wherein R is benzyl, phenoxymethyl, α-benzyloxycarbamoyl-benzyl or 2-ethoxynaphthyl and $Y_1$, $Y_2$ and $Y_3$ are chlorine, methyl or phenyl, or one of Y is methyl substituted with chlorine (preferably dichloromethyl) or a butyl (preferably t-butyl) group.

The 6-aminopenicillanic acid sulfoxide silyl esters of the formula I can be prepared in manner known per se for the preparation of esters. For example, a 6-aminopenicillanic acid sulfoxide of the formula

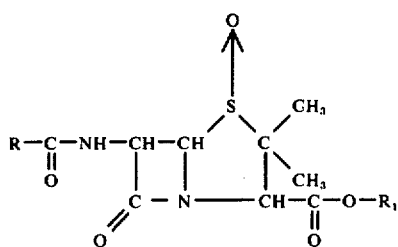

wherein R is as hereinbefore defined, and $R_1$ is hydrogen or a suitable cation, such as sodium, potassium or calcium, is reacted with a silicon-halogen compound of the formula

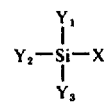

wherein $Y_1$, $Y_2$ and $Y_3$ are as hereinbefore defined but do not represent a 6-substituted aminopenicillanyl sulfoxide carbonyloxy group and X represents a halogen (preferably chlorine) atom, under anhydrous conditions and at room temperature, in the presence of at least one nitrogen-containing base, preferably in an inert organic medium.

Suitable nitrogen-containing bases are secondary or tertiary aliphatic, cycloaliphatic, aromatic or heterocyclic amines, preferably having a pKa value in water between 4 and 10. Particularly suitable are hexamethylenetetramine, N-methylaniline, dimethylaniline, pyridine and pyridine substituted by, for example, one or more lower alkyl or mono- or di-(lower) alkylamino groups, such as the picolines, 2-ethylpyridine, 2-propylpyridine, 2,3-dimethylpyridine, 2,5-dimethylpyridine, 2,6-dimethylpyridine, collidines and 2-dimethylaminopyridine, or quinoline or 3-methylisoquinoline. Preferred bases are α-picoline, 2,5-dimethylpyridine, 2-dimethylaminopyridine and 3-methylisoquinoline.

Examples of suitable silicon-halogen compounds of formula III are trimethylchlorosilane, dimethyldichlorosilane, triethylchlorosilane, methyltrichlorosilane, trimethylbromosilane, tri-n-propylchlorosilane, triethylbromosilane, tri-n-propyl-bromosilane, bromomethyl-dimethylchlorosilane, tri-n-butyl-chlorosilane, methyldiethylchlorosilane, dimethylethylchlorosilane, phenyldimethylbromosilane, phenylethylmethylchlorosilane, triphenylchlorosilane, dimethyl(t-butyl)-chlorosilane, (dichloromethyl)dimethylchlorosilane and methyldiphenylchlorosilane. Of the silicon compounds that are most widely used in chemistry, trimethylchlorosilane and dimethyldichlorosilane are preferred.

The process of the invention may be carried out in an inert organic solvent medium. Suitable solvents are acetonitrile, chlorobenzene, dimethylformamide, dioxane, nitrobenzene, anisole, benzene, carbon tetrachloride, and especially benzyl cyanide and halogenoalkanes such as 1,2-dichloroethane, 1,1-dichloroethane, 1-bromo-1-chloroethane, 1,2,3-trichloropropane and chloroform. The process can be carried out using the nitrogen-containing organic base (e.g. pyridine) itself as reaction medium. Good combinations of organic bases and solvents are α-picoline or 2,5-dimethylpyridine with benzyl cyanide or one of the above-mentioned halogenoalkanes, such as 1,2-dichloroethane, 1-bromo-1-chloroethane or chloroform.

The 6-aminopenicillanic sulfoxide derivatives of formula II employed as starting materials in the above process can be obtained by treatment of the corresponding 6-aminopenicillanic derivatives with an oxidizing agent by known methods. For this purpose, the 6-aminopenicillanic derivative is treated with a substance affording active oxygen such as sodium periodate, a peracid, hydrogen peroxide or iodosobenzene, in a proportion sufficient to oxidize the thiazolidine sulfur atom to an —SO— group. The initial compound can be the free acid or a salt thereof, suitably dissolved in a solvent which is inert under the reaction conditions used. The resulting sulfoxide can be readily recovered from the reaction mixture by methods known per se.

A preferred method is to start from an aminopenicillanic sulfoxide derivative, obtained from a penicillin which can easily be prepared by fermentation, such as benzylpenicillin or phenoxymethylpenicillin.

The new 6-aminopenicillanic acid sulfoxide silyl esters of the formula I can be employed as starting materials in the new process of preparing 7-aminodesacetoxy-cephalosporanic acid derivatives, which process is disclosed in parent patent application Ser. No. 115,883. In this process, a 6-aminopenicillanic acid sulfoxide silyl ester of formula I is heated under anhydrous conditions in the presence of at least one nitrogen-containing organic base and a silicon compound having a silicon-halogen bond, at least 5 moles of base being present for each mole of penicillanic sulfoxide, optionally in an inert organic medium. The same nitrogen-containing bases, silicon-halogen compounds and organic media as described hereinabove, may be used in this process.

The 7-aminodesacetoxycephalosporanic acid derivatives obtained with this process, possess useful antibiotic activity and are, therefore, very important as therapeutics.

In the following examples there are described several preferred embodiments to illustrate the invention. However, it should be understood that the invention is not intended to be limited to the specific embodiments.

EXAMPLE 1

Trimethylsilyl ester of 6-phenylacetamido-penicillanic acid sulfoxide

A solution of 1ml (7.2mmol) of triethylamine in 10 ml of carbon tetrachloride was added rapidly to a suspension of 2.5 g (7.15 mmol) of benzyl-penicillin sulfoxide in 30 ml of dry tetrachloromethane. After stirring for 15 minutes, a solution of 1 ml (7.9 mmol) of trimethylchlorosilane in 10 ml of tetrachloromethane was added slowly at room temperature and after further stirring for 90 minutes at room temperature, the reaction mixture was concentrated to a volume of about 20 ml and filtered. The precipitate containing triethylamine hydrochloride was washed three times with dry tetrachloromethane and from the combined filtered tetrachloromethane solutions, a PMR spectrum was recorded. The analysis of this spectrum was as follows:

PMR (in tetrachloromethane, values in ppm):
δ: 0.32 (s,9); 1.13 (s,3); 1.63 (s,3); 3.53 (s,2); 4.54 (s,1); 4.95 (d, 1, J = 5 Hz); 5.90 (q, 1, J = 5 Hz and 11 Hz); 7.27 (d, 1, J = 11 Hz); 7.30 (s,5).

Tetramethylsilane was used as an internal standard. By totally evaporating the filtrate to dryness, the trimethylsilyl ester of 6-phenylacetamidopenicillanic sulfoxide was obtained in an amorphous state.

EXAMPLE 2

Dimethylchlorosilyl ester and dimethylsilyl diester of phenoxymethylpenicillin sulfoxide 2.6 g (0.0072 mol) of phenoxymethylpenicillin sulfoxide, 1.75 ml (0.014 mol) of dimethyldichlorosilane and 17.2 ml (0.17 mol) of α-picoline were dissolved in 35 ml of 1,2-dichloroethane, and the solution was stirred for 1 hour at room temperature to form a mixture of the dimethylchlorosilyl ester of phenoxymethylpenicillin sulfoxide and di(phenoxymethylpenicillinsulfoxide) dimethylsilyl ester in situ.

The analysis of the PMR spectra of both components of this mixture were as follows: Phenoxymethylpenicillin sulfoxide dimethylchlorosilyl ester: δ: 0.59 (s,6); 1.30 (s,3); 1.73 (s,3); 4.55 (s,2); 4.76 (s,1); 5.28 (d, 1, J = 4.5 Hz); 6.15 (q,1, J = 11 and 4.5 Hz); 6.80–7.90 (m, 5); 8.30 (d, 1, J = 11 Hz).

Di(phenoxymethylpenicillin sulfoxide)dimethylsilyl ester: δ: 0.39 (s,6); 1.30 (s,3); 1.73 (s,3); 4.55 (s,2); 4.76 (s,1); 5.28 (d, 1, J = 4.5 Hz); 6.15 (q, 1, J = 11 and 4.5 Hz); 6.80–7.90 (m, 5); 8.30 (d, 1, J = 11 Hz). Tetramethylsilane was used as an internal reference.

EXAMPLE 3

Dimethylchlorosilyl ester and dimethylsilyl diester of 6-(α-benzyloxycarbamoylphenylacetamido)-penicillanic acid sulfoxide 2.6 g (0.0072 mol) of 6-(α-benzyloxycarbamoylphenylacetamido)-penicillanic acid sulfoxide (prepared by reaction of n-benzyloxycarbonylampicillin with periodic acid), 1.75 ml (0.014 mol) of dimethyldichlorosilane and 17.2 ml (0.17 mol) of α-picoline were dissolved in 35 ml of 1,2-dichloroethane and the mixture was stirred for 2 hours at room temperature. The analysis of the PMR spectra of the obtained 6-(α-benzyloxycarbamoylphenylacetamido) penicillin sulfoxide dimethylchlorosilyl ester (mono-ester) and of di [6-(α-benzyloxycarbamoylphenylacetamido)penicillin sulfoxide] dimethylsilyl ester (diester) were as follows:

Mono-ester: δ: 0.56 (s,6); 1.23 (s, 3); 1.68 (s, 3); 4.52 (s,1); 5.07 (d, 1, J = 4.5 Hz); 5.11 (s, 2); 5.46 (d, 1, J = 6 Hz); 6.00 (q, 1, J = 10 and 4.5 Hz); ca. 7.50 (m, 5); 8.15 (d, 1, J = 10 Hz).

Di-ester: δ: 0.35 (s, 6); 1.23 (s, 3); 1.68 (s, 3); 4.52 (s,1); 5.07 (d, 1, J = 4.5 Hz); 5.11 (s, 2); 5.46 (d, 1, J = 6 Hz); 6.00 (q, 1, J = 10 and 4.5 Hz); ca. 7.50 (m, 5); 8.15 (d, 1, J = 10 Hz).

Tetramethylsilane was used as an internal reference.

EXAMPLE 4

Trimethylsilyl ester of 2-ethoxy-naphthyl penicillin sulfoxide

A mixture of 2.6 g (6 mmol) of 2-ethoxynaphthyl-penicillin sulfoxide, 20 ml of chloroform, 20 ml (200 mmol) of α-picoline and 4.8 ml (36 mmol) of trimethylchlorosilane was stirred for 2 hours at room temperature. The analysis of the PMR spectrum of the obtained compound, 2-ethoxynaphthyl penicillin sulfoxide trimethylsilyl ester, was as follows (in mixture of $CDCl_3$ and DMSO):

δ: 0.32 (s, 9); 1.27 (s, 3); 1.44 (t, 3, J = 7 Hz); 1.66 (s,3); 4.19 (q, 2, J = 7 Hz); 4.54 (s,1); 5.24 (d, 1, J = 4.5 Hz); 6.28 (dd, 1, J = 11 Hz and 4.5 Hz); ca. 7.50 (m, 7). Tetramethylsilane was used as an internal reference.

EXAMPLE 5

Trimethylsilyl ester of phenoxymethylpenicillin sulfoxide

A mixture of 36.6 g (0.1 mole) of phenoxymethyl-penicillinsulfoxide, 360 ml (3.6 mole) of α-picoline and 81 ml (0.64 mole) of trimethylchlorosilane in 360 ml of chloroform was stirred at room temperature for 1 hour. The trimethylsiyl ester of phenoxymethylpenicillinsulfoxide was formed in situ.

The analysis of the PMR spectrum of the obtained compound (in a mixture of $CDCl_3$ and $d_5$-puridine) was as follows: δ: 0.34 (s, 9); 1.23 (s,3); 1.70 (s, 3); 4.49 (s, 2) 4.61 (s,1); 4.96 (d, 1, J = 4.5 Hz); 6.04 (q, 1, J = 11 and 4.5 Hz); 6.72–7.42 (m, 5); 8.15 (d, 1, J = 11 Hz). Tetramethylsilane was used as an internal reference.

EXAMPLE 6

Dimethyl(t-butyl)silyl ester of benzylpenicillin sulfoxide

To a solution of 10.5 g (30 mmoles) of benzylpenicillin sulfoxide and 4.2 ml (30 mmoles) of triethylamine in 50 ml of benzene was added a solution of 4.8ml (32 mmoles) of dimethyl (t-butyl) chlorosilane in 25 ml of benzene. After 1 hour, the precipitate formed was filtered off and the filtrate was concentrated to dryness to obtain 14.1 g of benzylpenicillin sulfoxide dimethyl (t-butyl)silyl ester.

PMR (benzene-d6; 60 Mc; δ-values in ppm; tetramethylsilane as an internal reference):

δ: 0.18 (s, 6); 0.79 (s, 3); 0.84 (s, 9); 1.43 (s, 3); 3.31 (s, 2); 4.11 (d, 1, J = 4.5 Hz); 4.75 (s, 1); 5.92 (dd, 1, J = 4.5 Hz and J = 10 Hz); 7.15 (s, 5); 7.38 (d, 1, J = 10 Hz).

EXAMPLE 7

(Dichloromethyl)dimethylsilyl ester of phenoxymethylpenicillin sulfoxide

A solution of 1.5 ml (10 mmoles) of (dichloromethyl) dimethylchlorosilane in 8.5 ml of benzene was added with stirring to a mixture of 3.7 g (10 mmoles) of phenoxymethylpenicillin sulfoxide, 1.4 ml (10 mmoles) of triethylamine and 15 ml of benzene. After stirring for half an hour, the mixture was concentrated to dryness and the residue consisted of phenoxymethylpenicillin sulfoxide (dichloromethyl)dimethylsilyl ester, contaminated with triethyl ammonium chloride.

PMR ($CDCl_3$; 60 Mc; δ-values in ppm; tetramethylsilane as an internal reference):

δ: 0.58 (s, 6); 1.31 (s, 3); 1.75 (s, 3); 4.52 (s, 2); 4.64 (s, 1); 5.08 (d, 1, J = 4.5 Hz); 5.54 (s, 1); 6.05 (dd, 1, J = 4.5 Hz and J = 10.5 Hz); 6.85–7.25 (m, 5); 8.27 (d, 1, J = 10.5 Hz).

EXAMPLE 8

Methyldiphenylsilyl ester of phenoxymethylpenicillin sulfoxide

A solution of 2.7 ml (10 mmoles) of methyldiphenylchlorosilane in 7 ml of benzene was added with stirring to a mixture of 3.7 g (10 mmoles) of phenoxymethylpenicillin sulfoxide, 1.4 ml (10 mmoles) of triethylamine and 15 ml of benzene. After stirring for half an hour; the solvent was evaporated in vacuo and carbon tetrachloride as added to the residue. After filtration, the filtrate was concentrated in vacuo and the residue consisted of phenoxymethylpenicillin sulfoxide methyldiphenylsilyl ester.

PMR ($CDCl_3$; 60 Mc; δ-values in ppm; tetramethylsilane as an internal reference):

δ: 0.92 (s, 3); 1.02 (s,3); 1.69 (s, 3); 4.52 (s, 2); 4.75 (s, 1); 4.95 (d, 1, J = 4.5 Hz); 6.05 (dd, 1, J = 4.5 Hz and J = 10.5 Hz); 6.82–7.75 (m, 15); 8.30 (d, 1, J = 10.5 Hz).

Various modifications of the products and process of the invention may be made without departing from the spirit or scope thereof and it is to be understood that the invention is intended to be limited only as defined in the appended claims.

I claim:

1. 6-aminopenicillanic acid sulfoxide silyl esters of the formula

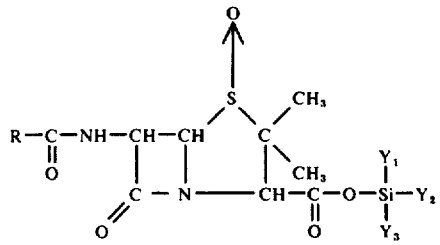

wherein R is selected from the group consisting of benzyl, phenyl (amino-methylene), phenyl (benzyloxycarbamoyl-methylene), phenoxy methyl, naphthyl and ethoxy-naphthyl and $Y_1$, $Y_2$ and $Y_3$ are individually selected from the group consisting of halogen, haloalkyl and alkyl of 1 to 4 carbon atom, phenyl and 6-substituted aminopenicillanyl sulfoxide carbonyloxy according to the group which is attached to the silicon atom in the above formula, wherein R is as hereinbefore defined.

2. A 6-aminopenicillanic acid sulfoxide silyl ester of claim 1 wherein R is selected from the group consisting of benzyl, phenoxymethyl, α-benzyloxycarbamoyl-benzyl and 2-ethoxy-naphthyl.

3. A 6-aminopenicillanic acid sulfoxide silyl ester of claim 1 wherein $Y_1$, $Y_2$ and $Y_3$ are selected from the group consisting of chlorine, methyl, chloromethyl, phenyl and butyl.

4. A compound of claim 1 which is 6-phenylacetamidopenicillanic sulfoxide trimethylsilyl ester.

5. A compound of claim 1 which is phenoxymethylpenicillin sulfoxide dimethylchlorosilyl ester.

6. A compound of claim 1 which is di(phenoxymethylpenicillinsulfoxide) dimethylsilyl ester.

7. A compound of claim 1 which is 6-(α-benzyloxycarbamoyl phenylacetamido) penicillin sulfoxide dimethylchlorosilyl ester.

8. A compound of claim 1 which is di [6-(α-benzyloxycarbamoyl-phenylacetamido) penicillin sulfoxide] dimethylsilyl ester.

9. A compound of claim 1 which is 2-ethoxy-naphthyl penicillin sulfoxide trimethylsilyl ester.

10. A compound of claim 1 which is phenoxymethylpenicillin sulfoxide trimethylsilyl ester.

11. A compound of claim 1 which is benzylpenicillin sulfoxide dimethyl(t-butyl) silyl ester.

12. A compound of claim 1 which is phenoxymethylpenicillin sulfoxide (dichloromethyl)dimethylsilyl ester.

13. A compound of claim 1 which is phenoxymethylpenicillin sulfoxide methyldiphenylsilyl ester.

* * * * *